United States Patent [19]
Snyder et al.

[11] Patent Number: 5,632,989
[45] Date of Patent: May 27, 1997

[54] ATTENUATED, LIVE VACCINE FOR DELAWARE STRAIN IBDV

[75] Inventors: David B. Snyder; Vikram Vakharia, both of Bowie, Md.; Heinrich D. Luetticken, Boxmeer, Netherlands

[73] Assignee: University of Maryland, College Park, Md.

[21] Appl. No.: 944,525

[22] Filed: Sep. 15, 1992

Related U.S. Application Data

[63] Continuation-in-part of Ser. No. 423,758, Oct. 18, 1989, abandoned.
[51] Int. Cl.⁶ .......................... A61K 39/42; A61K 39/12; C12N 7/04; C12N 5/18
[52] U.S. Cl. .......................... 424/139.1; 424/147.1; 424/204.1; 435/235.1; 435/236; 435/331; 435/339; 530/387.9; 530/388.3
[58] Field of Search .......................... 424/88, 89, 93 A, 424/93 T, 184.1–186.1, 204.1, 139.1, 147.1; 435/69.3, 237, 172.3, 235.1, 236, 320.1, 252.3, 240.27; 536/23.72, 23.1; 530/388.3, 387.9

[56] References Cited

U.S. PATENT DOCUMENTS

| | | | |
|---|---|---|---|
| 4,530,831 | 7/1985 | Lütticken et al. | 424/202.1 |
| 4,824,668 | 4/1989 | Melchior et al. | 424/202.1 |
| 4,956,452 | 9/1990 | Snyder et al. | 424/147.1 |
| 5,064,646 | 11/1991 | Snyder | 424/147.1 |

FOREIGN PATENT DOCUMENTS

| | | | |
|---|---|---|---|
| 86/07060 | 12/1986 | WIPO | C07H 21/04 |
| 9116925 | 11/1991 | WIPO | |

OTHER PUBLICATIONS

Snyder, D.B. et al. Avian Diseases 32:527–534 (1988).
Bayless, C.D. et al. J. Gen Virology 71:1303–1312 (1990).
Kumar, V. et al. Proc. Natl. Acad. Sci. USA 87:1337–1341 (1990).
Spies, U. et al. Nucleic Acids Research 17(19):7982 (1989).
Kibenge, F.S.B et al. J. Gen. Virol 71:569–577 (1990).
Bayliss, C.D. et al. J. Gen. Virol 71:1303–1312 (1990).
Bowie, A.U. et al. Science 247:1306–1310 (1990).
Virology, vol. 184, issued Sep. 1991, pp. 437–440, F.S.B. Kibenge, et al., "Genome Cloning and Analysis of the Large RNA Segment (Segment A) of a Naturally Avirulent Serotype 2 Infectious Bursal Disease Virus".
Journal of General Virology, vol. 72, issued Aug. 1991, pp. 1835–1843, H.G. Heine, et al., "Sequence Analysis and Expression of the Host–Protective Immunogen VP2 of a Variant Strain of Infectious Bursal Disease Virus Which Can Circumvent Vaccination with Standard Type 1 Strains".

*Primary Examiner*—Mary E. Mosher
*Attorney, Agent, or Firm*—Oblon, Spivak, McClelland, Maier & Neustadt, P.C.

[57] ABSTRACT

Live, attenuated Delaware infectious bursal disease viruses are screened for effectiveness by a monoclonal antibody specific for said Delaware strain. Those which are not bound by the antibody are not or may not be as effective in conferring protection against homologous wild type infectious bursal disease infection. Currently available live, attenuated vaccines do not include a virus having the binding site specified. A monoclonal antibody specific for the Delaware strain also provides a vaccine for passive immunization.

8 Claims, 6 Drawing Sheets

```
        10          20          30          40          50
         |           |           |           |           |
GAA TTC CTC CTT CTA CAA CGC TAT CAT TGA TGG TTA GTA GAG ATC AGA CAA ACG
--- --- --- --- --- --- --- --- --- --- --- --- --- --- --- --- --- ---

60          70          80          90         100
     |           |           |           |           |
ATC GCA GCG ATG ACA AAC CTG CAA GAT CAA ACC CAC CAG ATT GTT CCG TTC ATA
--- --- --- MET Thr Asn Leu Gln Asp Gln Thr His Gln Ile Val Pro Phe Ile 110         120         130         140         150         160
 |           |           |           |           |           |
CGG AGC CTT CTG ATG CCA ACA ACC GGA CCG GCG TCC ATT CCG GAC GAC ACC CTG
Arg Ser Leu Leu MET Pro Thr Thr Gly Pro Ala Ser Ile Pro Asp Asp Thr Leu 170         180         190         200         210
     |           |           |           |           |
GAG AAG CAC ACT CTC AGG TCA GAG ACC TCG ACC TAC AAT TTG ACT GTG GGG GAC
Glu Lys His Thr Leu Arg Ser Glu Thr Ser Thr Tyr Asn Leu Thr Val Gly Asp 220         230         240         250         260         270
 |           |           |           |           |           |
ACA GGG TCA GGG CTA ATT GTC TTT TTC CCT GGA TTC CCT GGC TCA ATT GTG GGT
Thr Gly Ser Gly Leu Ile Val Phe Phe Pro Gly Phe Pro Gly Ser Ile Val Gly 280         290         300         310         320
         |           |           |           |           |
GCT CAC TAC ACA CTG CAG AGC AGT GGG AAC TAC AAG TTC GAT CAG ATG CTC CTG
Ala His Tyr Thr Leu Gln Ser Ser Gly Asn Tyr Lys Phe Asp Gln MET Leu Leu 330         340         350         360         370
     |           |           |           |           |
ACT GCC CAG AAC CTA CCG GCC AGC TAC AAC TAC TGC AGG CTA GTG AGT CGG AGT
Thr Ala Gln Asn Leu Pro Ala Ser Tyr Asn Tyr Cys Arg Leu Val Ser Arg Ser 380         390         400         410         420         430
 |           |           |           |           |           |
CTC ACA GTA AGG TCA AGC ACA CTC CCT GGT GGC GTT TAT GCA CTA AAC GGC ACC
Leu Thr Val Arg Ser Ser Thr Leu Pro Gly Gly Val Tyr Ala Leu Asn Gly Thr
```

*FIG. 1*

```
        440              450              460              470              480
         |                |                |                |                |
ATA AAC GCC GTG ACC TTC CAA GGA AGC CTG AGT GAA CTG ACA GAT GTT AGC TAC
Ile Asn Ala Val Thr Phe Gln Gly Ser Leu Ser Glu Leu Thr Asp Val Ser Tyr 490              500              510              520              530              540
         |                |                |                |                |                |
AAC GGG TTG ATG TCT GCA ACA GCC AAC ATC AAC GAC AAA ATT GGG AAC GTC CTA
Asn Gly Leu MET Ser Ala Thr Ala Asn Ile Asn Asp Lys Ile Gly Asn Val Leu 550              560              570              580              590
              |                |                |                |                |
GTA GGG GAA GGG GTA ACC GTC CTC AGC TTA CCC ACA TCA TAT GAT CTT GGG TAT
Val Gly Glu Gly Val Thr Val Leu Ser Leu Pro Thr Ser Tyr Asp Leu Gly Tyr 600              610              620              630              640
         |                |                |                |                |
GTG AGG CTT GGT GAC CCC ATA CCC GCT ATA GGG CTT GAC CCA AAA ATG GTA GCA
Val Arg Leu Gly Asp Pro Ile Pro Ala Ile Gly Leu Asp Pro Lys MET Val Ala 650              660              670              680              690              700
 |                |                |                |                |                |
ACA TGT GAC AGC AGT GAC AGG CCC AGA GTC TAC ACC ATA ACT GCA GCC GAT AAT
Thr Cys Asp Ser Ser Asp Arg Pro Arg Val Tyr Thr Ile Thr Ala Ala Asp Asn 710              720              730              740              750
         |                |                |                |                |
TAC CAA TTC TCA TCA CAG TAC CAA ACA GGT GGG GTA ACA ATC ACA CTG TTC TCA
Tyr Gln Phe Ser Ser Gln Tyr Gln Thr Gly Gly Val Thr Ile Thr Leu Phe Ser 760              770              780              790              800              810
         |                |                |                |                |                |
GCC AAC ATT GAT GCC ATC ACA AGT CTC AGC GTT GGG GGA GAG CTC GTG TTC AAA
Ala Asn Ile Asp Ala Ile Thr Ser Leu Ser Val Gly Gly Glu Leu Val Phe Lys 820              830              840              850              860
         |                |                |                |                |
ACA AGC GTC CAA AGC CTT GTA CTG GGC GCC ACC ATC TAC CTT ATA GGC TTT GAT
Thr Ser Val Gln Ser Leu Val Leu Gly Ala Thr Ile Tyr Leu Ile Gly Phe Asp 870              880              890              900              910
         |                |                |                |                |
GGG ACT GCG GTA ATC ACC AGA GCT GTG GCC GCA AAC AAT GGG CTG ACG GCC GGC
Gly Thr Ala Val Ile Thr Arg Ala Val Ala Ala Asn Asn Gly Leu Thr Ala Gly 920              930              940              950              960              970
 |                |                |                |                |                |
ATC GAC AAT CTT ATG CCA TTC AAT CTT GTG ATT CCA ACC AAT GAG ATA ACC CAG
Ile Asp Asn Leu MET Pro Phe Asn Leu Val Ile Pro Thr Asn Glu Ile Thr Gln 980              990             1000             1010             1020
         |                |                |                |                |
CCA ATC ACA TCC ATC ATA CTG GAG ATA GTG ACC TCC AAA AGT GAT GGT CAG GCA
Pro Ile Thr Ser Ile Ile Leu Glu Ile Val Thr Ser Lys Ser Asp Gly Gln Ala
```

*FIG. 1A*

```
    1030         1040         1050         1060         1070         1080
     |            |            |            |            |            |
GGG GAA CAG ATG TCA TGG TCG GCA AGT GGG AGC CTA GCA GTG ACG ATC CAT GGT
Gly Glu Gln MET Ser Trp Ser Ala Ser Gly Ser Leu Ala Val Thr Ile His Gly 1090         1100         1110         1120         1130
           |            |            |            |            |
  GGC AAC TAT CCA GGA GCC CTC CGT CCC GTC ACA CTA GTG GCC TAC GAA AGA GTG
  Gly Asn Tyr Pro Gly Ala Leu Arg Pro Val Thr Leu Val Ala Tyr Glu Arg Val 1140         1150         1160         1170         1180
      |            |            |            |            |
GCA ACA GGA TCT GTC GTT ACG GTC GCT GGG GTG AGC AAC TTC GAG CTG ATC CCA
Ala Thr Gly Ser Val Val Thr Val Ala Gly Val Ser Asn Phe Glu Leu Ile Pro 1190         1200         1210         1220         1230         1240
 |            |            |            |            |            |
AAT CCT GAA CTA GCA AAG AAC CTG GTT ACA GAA TAC GGC CGA TTT GAC CCA GGA
Asn Pro Glu Leu Ala Lys Asn Leu Val Thr Glu Tyr Gly Arg Phe Asp Pro Gly 1250         1260         1270         1280         1290
           |            |            |            |            |
  GCC ATG AAC TAC ACG AAA TTG ATA CTG AGT GAG AGG GAC CAC CTT GGC ATC AAG
  Ala MET Asn Tyr Thr Lys Leu Ile Leu Ser Glu Arg Asp His Leu Gly Ile Lys 1300         1310         1320         1330         1340         1350
      |            |            |            |            |            |
ACC GTC TGG CCA ACA AGG GAG TAC ACT GAC TTT CGT GAG TAC TTC ATG GAG GTG
Thr Val Trp Pro Thr Arg Glu Tyr Thr Asp Phe Arg Glu Tyr Phe MET Glu Val 1360         1370         1380         1390         1400
           |            |            |            |            |
  GCC GAC CTC AAC TCT CCC CTG AAG ATT GCA GGA GCA TTT GGC TTC AAA GAC ATA
  Ala Asp Leu Asn Ser Pro Leu Lys Ile Ala Gly Ala Phe Gly Phe Lys Asp Ile 1410         1420         1430         1440         1450
      |            |            |            |            |
ATC CGG GCC ATA AGG AGG ATA GCT GTA CCG GTG GTC TCT ACA TTG TTC CCA CCT
Ile Arg Ala Ile Arg Arg Ile Ala Val Pro Val Val Ser Thr Leu Phe Pro Pro 1460         1470         1480         1490         1500         1510
 |            |            |            |            |            |
GCC GCT CCT CTA GCC CAT GCA ATT GGG GAA GGT GTA GAC TAC CTA CTG GGC GAT
Ala Ala Pro Leu Ala His Ala Ile Gly Glu Gly Val Asp Tyr Leu Leu Gly Asp 1520         1530         1540         1550         1560
           |            |            |            |            |
  GAG GCA CAG GCT GCT TCA GGA ACC GCT CGA GCC GCG TCA GGA AAA GCA AGG GCT
  Glu Ala Gln Ala Ala Ser Gly Thr Ala Arg Ala Ala Ser Gly Lys Ala Arg Ala 1570         1580         1590         1600         1610         1620
      |            |            |            |            |            |
GCC TCA GGC CGC ATA AGG CAG CTG ACT CTC GCC GCC GAC AAG GGG TAC GAG GTA
Ala Ser Gly Arg Ile Arg Gln Leu Thr Leu Ala Ala Asp Lys Gly Tyr Glu Val
```

*FIG. 1B*

```
        1630            1640            1650            1660            1670
         |               |               |               |               |
GTC GCG AAT CTA TTC CAG GTG CCC CAG AAT CCC GTA GTC GAC GGG ATT CTT GCT
Val Ala Asn Leu Phe Gln Val Pro Gln Asn Pro Val Val Asp Gly Ile Leu Ala 1680            1690            1700            1710            1720
         |               |               |               |               |
TCA CCC GGG ATA CTT CGC GGT GCA CAC AAC CTC GAC TGC GTG CTA AGA GAG GGT
Ser Pro Gly Ile Leu Arg Gly Ala His Asn Leu Asp Cys Val Leu Arg Glu Gly 1730            1740            1750            1760            1770            1780
   |               |               |               |               |               |
GCC ACG CTA TTC CCT GTG GTC ATT ACG ACA GTG GAA GAC GCC ATG ACA CCC AAA
Ala Thr Leu Phe Pro Val Val Ile Thr Thr Val Glu Asp Ala MET Thr Pro Lys 1790            1800            1810            1820            1830
         |               |               |               |               |
GCA CTG AAC AGC AAA ATG TTT GCT GTC ATT GAA GGC GTG CGA GAA GAC CTC CAA
Ala Leu Asn Ser Lys MET Phe Ala Val Ile Glu Gly Val Arg Glu Asp Leu Gln 1840            1850            1860            1870            1880            1890
   |               |               |               |               |               |
CCT CCA TCT CAA AGA GGA TCC TTC ATA CGA ACT CTC TCC GGA CAC AGA GTC TAT
Pro Pro Ser Gln Arg Gly Ser Phe Ile Arg Thr Leu Ser Gly His Arg Val Tyr 1900            1910            1920            1930            1940
         |               |               |               |               |
GGA TAT GCT CCA GAT GGG GTA CTT CCA CTG GAG ACT GGG AGA GAC TAC ACC GTT
Gly Tyr Ala Pro Asp Gly Val Leu Pro Leu Glu Thr Gly Arg Asp Tyr Thr Val 1950            1960            1970            1980            1990
         |               |               |               |               |
GTC CCA ATA GAT GAT GTC TGG GAC GAC AGC ATT ATG CTG TCC AAG GAC CCC ATA
Val Pro Ile Asp Asp Val Trp Asp Asp Ser Ile MET Leu Ser Lys Asp Pro Ile 2000            2010            2020            2030            2040            2050
   |               |               |               |               |               |
CCT CCT ATT GTG GGA AAC AGT GGA AAC CTA GCC ATA GCT TAC ATG GAT GTG TTT
Pro Pro Ile Val Gly Asn Ser Gly Asn Leu Ala Ile Ala Tyr MET Asp Val Phe 2060            2070            2080            2090            2100
         |               |               |               |               |
CGA CCC AAA GTC CCC ATC CAT GTG GCC ATG ACG GGA GCC CTC AAC GCT TGT GGC
Arg Pro Lys Val Pro Ile His Val Ala MET Thr Gly Ala Leu Asn Ala Cys Gly 2110            2120            2130            2140            2150            2160
   |               |               |               |               |               |
GAG ATT GAG AAA ATA AGC TTC AGA AGC ACC AAG CTC GCC ACC GCA CAC CGG CTT
Glu Ile Glu Lys Ile Ser Phe Arg Ser Thr Lys Leu Ala Thr Ala His Arg Leu 2170            2180            2190            2200            2210
         |               |               |               |               |
GGC CTC AAG TTG GCT GGT CCC GGA GCA TTC GAT GTA AAC ACC GGG CCC AAC TGG
Gly Leu Lys Leu Ala Gly Pro Gly Ala Phe Asp Val Asn Thr Gly Pro Asn Trp
```

*FIG. 1C*

```
                2220            2230           2240           2250            2260
                 |               |              |              |               |
        GCA ACG TTC ATC AAA CGT TTC CCT CAC AAT CCA CGC GAC TGG GAC AGG CTC CCC
        Ala Thr Phe Ile Lys Arg Phe Pro His Asn Pro Arg Asp Trp Asp Arg Leu Pro
         2270            2280           2290           2300            2310           2320
          |               |              |              |               |              |
        TAC CTT AAC CTT CCA TAC CTT CCA CCC AAT GCA GGA CGC CAG TAC CAC CTT GCC
        Tyr Leu Asn Leu Pro Tyr Leu Pro Pro Asn Ala Gly Arg Gln Tyr His Leu Ala
                     2330            2340           2350           2360           2370
                      |               |              |              |              |
        ATG GCT GCA TCA GAG TTC AAA GAG ACC CCT GAA CTC GAG AGC GCC GTA AGA GCC
        MET Ala Ala Ser Glu Phe Lys Glu Thr Pro Glu Leu Glu Ser Ala Val Arg Ala
             2380            2390           2400           2410           2420           2430
              |               |              |              |              |              |
        ATG GAA GCA GCT GCC AAT GTG GAC CCA CTG TTC CAA TCT GCA CTC AGT GTG TTC
        MET Glu Ala Ala Ala Asn Val Asp Pro Leu Phe Gln Ser Ala Leu Ser Val Phe
                     2440            2450           2460           2470           2480
                      |               |              |              |              |
        ATG TGG CTG GAA GAG AAT GGG ATT GTG ACT GAC ATG GCC AAC TTC GCA CTC AGC
        MET Trp Leu Glu Glu Asn Gly Ile Val Thr Asp MET Ala Asn Phe Ala Leu Ser
             2490            2500           2510           2520           2530
              |               |              |              |              |
        GAC CCG AAT GCC CAT CGG ATG CGA AAT TTT CTT GCA AAC GCA CCA CAA GCA GGC
        Asp Pro Asn Ala His Arg MET Arg Asn Phe Leu Ala Asn Ala Pro Gln Ala Gly
        2540            2550           2560           2570           2580           2590
         |               |              |              |              |              |
        AGC AAG TCG CAA AGG GCC AAG TAC GGG ACA GCA GGC TAC GGA GTG GAG GCC CGG
        Ser Lys Ser Gln Arg Ala Lys Tyr Gly Thr Ala Gly Tyr Gly Val Glu Ala Arg
                     2600            2610           2620           2630           2640
                      |               |              |              |              |
        GGC CCC ACA CCA GAG GAA GCA CAG AGG GAA AAA GAC ACA CGG ATC TCA AAG AAG
        Gly Pro Thr Pro Glu Glu Ala Gln Arg Glu Lys Asp Thr Arg Ile Ser Lys Lys
             2650            2660           2670           2680           2690           2700
              |               |              |              |              |              |
        ATG GAG ACC ATG GGC ATC TAC TTT GCA ACA CCA GAA TGG GTA GCA CTC AAT GGG
        MET Glu Thr MET Gly Ile Tyr Phe Ala Thr Pro Glu Trp Val Ala Leu Asn Gly
                     2710            2720           2730           2740           2750
                      |               |              |              |              |
        CAC CGC GGG CCA AGC CCC GGC CAG CTA AAG TAC TGG CAG AAC ACA CGA GAA ATA
        His Arg Gly Pro Ser Pro Gly Gln Leu Lys Tyr Trp Gln Asn Thr Arg Glu Ile
             2760            2770           2780           2790           2800
              |               |              |              |              |
        CCG GAC CCA AAC GAG GAC TAT CTA GAC TAC GTG CAT GCA GAG AAG AGC CGG TTG
        Pro Asp Pro Asn Glu Asp Tyr Leu Asp Tyr Val His Ala Glu Lys Ser Arg Leu
```

*FIG. 1D*

```
2810            2820            2830            2840            2850            2860
 |               |               |               |               |               |
GCA TCA GAA GAA CAA ATC CTA AGG GCA GCT ACG TCG ATC TAC GGG GCT CCA GGA
Ala Ser Glu Glu Gln Ile Leu Arg Ala Ala Thr Ser Ile Tyr Gly Ala Pro Gly 2870            2880            2890            2900            2910
        |               |               |               |               |
CAG GCA GAG CCA CCC CAA GCT TTC ATA GAC GAA GTT GCC AAA GTC TAT GAA ATC
Gln Ala Glu Pro Pro Gln Ala Phe Ile Asp Glu Val Ala Lys Val Tyr Glu Ile 2920            2930            2940            2950            2960            2970
 |               |               |               |               |               |
AAC CAT GGA CGT GGC CCA AAC CAA GGA CAG ATG AAA GAT CTG CTC TTG ACT GCG
Asn His Gly Arg Gly Pro Asn Gln Gly Gln MET Lys Asp Leu Leu Leu Thr Ala 2980            2990            3000            3010            3020
        |               |               |               |               |
ATG GAG ATG AAG CAT CGC AAT CCC AGG CGG GCT CCA CCA AAG CCC AAG CCA AAA
MET Glu MET Lys His Arg Asn Pro Arg Arg Ala Pro Pro Lys Pro Lys Pro Lys 3030            3040            3050            3060            3070
        |               |               |               |               |
CCC AAT GCT CCA ACA CAG AGA CCC CCT GGT CGG CTG GGC CGC TGG ATC AGG ACT
Pro Asn Ala Pro Thr Gln Arg Pro Pro Gly Arg Leu Gly Arg Trp Ile Arg Thr 3080            3090            3100            3110            3120            3130
 |               |               |               |               |               |
GTC TCT GAT GAG GAC CTT GAG TGA GGC TCC TGG GAG TCT CCC GAC ACC ACC CGC
Val Ser Asp Glu Asp Leu Glu --- --- --- --- --- --- --- --- --- --- ---

3140            3150            3160            3170            3180
        |               |               |               |               |
GCA GGC GTG GAC ACC AAT TCG GCC TTA CAA CAT CCC AAA TTG GAT CCG
--- --- --- --- --- --- --- --- --- --- --- --- --- --- --- ---
```

*FIG. 1E*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3180 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 64..3099

( x i ) SEQUENCE DESCRIPTION: SEQ ID NO:1:

```
GAATTCCTCC TTCTACAACG CTATCATTGA TGGTTAGTAG AGATCAGACA AACGATCGCA           60

GCG ATG ACA AAC CTG CAA GAT CAA ACC CAC CAG ATT GTT CCG TTC ATA          108
    Met Thr Asn Leu Gln Asp Gln Thr His Gln Ile Val Pro Phe Ile
    1               5                  10                  15

CGG AGC CTT CTG ATG CCA ACA ACC GGA CCG GCG TCC ATT CCG GAC GAC          156
Arg Ser Leu Leu Met Pro Thr Thr Gly Pro Ala Ser Ile Pro Asp Asp
                20                  25                  30

ACC CTG GAG AAG CAC ACT CTC AGG TCA GAG ACC TCG ACC TAC AAT TTG          204
Thr Leu Glu Lys His Thr Leu Arg Ser Glu Thr Ser Thr Tyr Asn Leu
            35                  40                  45

ACT GTG GGG GAC ACA GGG TCA GGG CTA ATT GTC TTT TTC CCT GGA TTC          252
Thr Val Gly Asp Thr Gly Ser Gly Leu Ile Val Phe Phe Pro Gly Phe
        50                  55                  60

CCT GGC TCA ATT GTG GGT GCT CAC TAC ACA CTG CAG AGC AGT GGG AAC          300
Pro Gly Ser Ile Val Gly Ala His Tyr Thr Leu Gln Ser Ser Gly Asn
    65                  70                  75

TAC AAG TTC GAT CAG ATG CTC CTG ACT GCC CAG AAC CTA CCG GCC AGC          348
Tyr Lys Phe Asp Gln Met Leu Leu Thr Ala Gln Asn Leu Pro Ala Ser
80                  85                  90                  95

TAC AAC TAC TGC AGG CTA GTG AGT CGG AGT CTC ACA GTA AGG TCA AGC          396
Tyr Asn Tyr Cys Arg Leu Val Ser Arg Ser Leu Thr Val Arg Ser Ser
                100                 105                 110

ACA CTC CCT GGT GGC GTT TAT GCA CTA AAC GGC ACC ATA AAC GCC GTG          444
Thr Leu Pro Gly Gly Val Tyr Ala Leu Asn Gly Thr Ile Asn Ala Val
                115                 120                 125

ACC TTC CAA GGA AGC CTG AGT GAA CTG ACA GAT GTT AGC TAC AAC GGG          492
Thr Phe Gln Gly Ser Leu Ser Glu Leu Thr Asp Val Ser Tyr Asn Gly
            130                 135                 140

TTG ATG TCT GCA ACA GCC AAC ATC AAC GAC AAA ATT GGG AAC GTC CTA          540
Leu Met Ser Ala Thr Ala Asn Ile Asn Asp Lys Ile Gly Asn Val Leu
        145                 150                 155

GTA GGG GAA GGG GTA ACC GTC CTC AGC TTA CCC ACA TCA TAT GAT CTT          588
Val Gly Glu Gly Val Thr Val Leu Ser Leu Pro Thr Ser Tyr Asp Leu
160                 165                 170                 175

GGG TAT GTG AGG CTT GGT GAC CCC ATA CCC GCT ATA GGG CTT GAC CCA          636
Gly Tyr Val Arg Leu Gly Asp Pro Ile Pro Ala Ile Gly Leu Asp Pro
                180                 185                 190

AAA ATG GTA GCA ACA TGT GAC AGC AGT GAC AGG CCC AGA GTC TAC ACC          684
Lys Met Val Ala Thr Cys Asp Ser Ser Asp Arg Pro Arg Val Tyr Thr
                195                 200                 205

ATA ACT GCA GCC GAT AAT TAC CAA TTC TCA TCA CAG TAC CAA ACA GGT          732
Ile Thr Ala Ala Asp Asn Tyr Gln Phe Ser Ser Gln Tyr Gln Thr Gly
```

```
              210                            215                            220
GGG  GTA  ACA  ATC  ACA  CTG  TTC  TCA  GCC  AAC  ATT  GAT  GCC  ATC  ACA  AGT       780
Gly  Val  Thr  Ile  Thr  Leu  Phe  Ser  Ala  Asn  Ile  Asp  Ala  Ile  Thr  Ser
     225                 230                           235

CTC  AGC  GTT  GGG  GGA  GAG  CTC  GTG  TTC  AAA  ACA  AGC  GTC  CAA  AGC  CTT       828
Leu  Ser  Val  Gly  Gly  Glu  Leu  Val  Phe  Lys  Thr  Ser  Val  Gln  Ser  Leu
240                      245                      250                      255

GTA  CTG  GGC  GCC  ACC  ATC  TAC  CTT  ATA  GGC  TTT  GAT  GGG  ACT  GCG  GTA       876
Val  Leu  Gly  Ala  Thr  Ile  Tyr  Leu  Ile  Gly  Phe  Asp  Gly  Thr  Ala  Val
                    260                      265                      270

ATC  ACC  AGA  GCT  GTG  GCC  GCA  AAC  AAT  GGG  CTG  ACG  GCC  GGC  ATC  GAC       924
Ile  Thr  Arg  Ala  Val  Ala  Ala  Asn  Asn  Gly  Leu  Thr  Ala  Gly  Ile  Asp
               275                      280                 285

AAT  CTT  ATG  CCA  TTC  AAT  CTT  GTG  ATT  CCA  ACC  AAT  GAG  ATA  ACC  CAG       972
Asn  Leu  Met  Pro  Phe  Asn  Leu  Val  Ile  Pro  Thr  Asn  Glu  Ile  Thr  Gln
          290                      295                      300

CCA  ATC  ACA  TCC  ATC  ATA  CTG  GAG  ATA  GTG  ACC  TCC  AAA  AGT  GAT  GGT      1020
Pro  Ile  Thr  Ser  Ile  Ile  Leu  Glu  Ile  Val  Thr  Ser  Lys  Ser  Asp  Gly
     305                 310                      315

CAG  GCA  GGG  GAA  CAG  ATG  TCA  TGG  TCG  GCA  AGT  GGG  AGC  CTA  GCA  GTG      1068
Gln  Ala  Gly  Glu  Gln  Met  Ser  Trp  Ser  Ala  Ser  Gly  Ser  Leu  Ala  Val
320                      325                      330                      335

ACG  ATC  CAT  GGT  GGC  AAC  TAT  CCA  GGA  GCC  CTC  CGT  CCC  GTC  ACA  CTA      1116
Thr  Ile  His  Gly  Gly  Asn  Tyr  Pro  Gly  Ala  Leu  Arg  Pro  Val  Thr  Leu
                    340                      345                      350

GTG  GCC  TAC  GAA  AGA  GTG  GCA  ACA  GGA  TCT  GTC  GTT  ACG  GTC  GCT  GGG      1164
Val  Ala  Tyr  Glu  Arg  Val  Ala  Thr  Gly  Ser  Val  Val  Thr  Val  Ala  Gly
               355                      360                      365

GTG  AGC  AAC  TTC  GAG  CTG  ATC  CCA  AAT  CCT  GAA  CTA  GCA  AAG  AAC  CTG      1212
Val  Ser  Asn  Phe  Glu  Leu  Ile  Pro  Asn  Pro  Glu  Leu  Ala  Lys  Asn  Leu
          370                      375                      380

GTT  ACA  GAA  TAC  GGC  CGA  TTT  GAC  CCA  GGA  GCC  ATG  AAC  TAC  ACG  AAA      1260
Val  Thr  Glu  Tyr  Gly  Arg  Phe  Asp  Pro  Gly  Ala  Met  Asn  Tyr  Thr  Lys
     385                      390                      395

TTG  ATA  CTG  AGT  GAG  AGG  GAC  CAC  CTT  GGC  ATC  AAG  ACC  GTC  TGG  CCA      1308
Leu  Ile  Leu  Ser  Glu  Arg  Asp  His  Leu  Gly  Ile  Lys  Thr  Val  Trp  Pro
400                      405                      410                      415

ACA  AGG  GAG  TAC  ACT  GAC  TTT  CGT  GAG  TAC  TTC  ATG  GAG  GTG  GCC  GAC      1356
Thr  Arg  Glu  Tyr  Thr  Asp  Phe  Arg  Glu  Tyr  Phe  Met  Glu  Val  Ala  Asp
                    420                      425                      430

CTC  AAC  TCT  CCC  CTG  AAG  ATT  GCA  GGA  GCA  TTT  GGC  TTC  AAA  GAC  ATA      1404
Leu  Asn  Ser  Pro  Leu  Lys  Ile  Ala  Gly  Ala  Phe  Gly  Phe  Lys  Asp  Ile
               435                      440                      445

ATC  CGG  GCC  ATA  AGG  AGG  ATA  GCT  GTA  CCG  GTG  GTC  TCT  ACA  TTG  TTC      1452
Ile  Arg  Ala  Ile  Arg  Arg  Ile  Ala  Val  Pro  Val  Val  Ser  Thr  Leu  Phe
          450                      455                      460

CCA  CCT  GCC  GCT  CCT  CTA  GCC  CAT  GCA  ATT  GGG  GAA  GGT  GTA  GAC  TAC      1500
Pro  Pro  Ala  Ala  Pro  Leu  Ala  His  Ala  Ile  Gly  Glu  Gly  Val  Asp  Tyr
465                      470                      475

CTA  CTG  GGC  GAT  GAG  GCA  CAG  GCT  GCT  TCA  GGA  ACC  GCT  CGA  GCC  GCG      1548
Leu  Leu  Gly  Asp  Glu  Ala  Gln  Ala  Ala  Ser  Gly  Thr  Ala  Arg  Ala  Ala
480                      485                           490                 495

TCA  GGA  AAA  GCA  AGG  GCT  GCC  TCA  GGC  CGC  ATA  AGG  CAG  CTG  ACT  CTC      1596
Ser  Gly  Lys  Ala  Arg  Ala  Ala  Ser  Gly  Arg  Ile  Arg  Gln  Leu  Thr  Leu
               500                      505                      510

GCC  GCC  GAC  AAG  GGG  TAC  GAG  GTA  GTC  GCG  AAT  CTA  TTC  CAG  GTG  CCC      1644
Ala  Ala  Asp  Lys  Gly  Tyr  Glu  Val  Val  Ala  Asn  Leu  Phe  Gln  Val  Pro
          515                      520                      525

CAG  AAT  CCC  GTA  GTC  GAC  GGG  ATT  CTT  GCT  TCA  CCC  GGG  ATA  CTT  CGC      1692
Gln  Asn  Pro  Val  Val  Asp  Gly  Ile  Leu  Ala  Ser  Pro  Gly  Ile  Leu  Arg
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 530 |     |     |     |     | 535 |     |     |     |     | 540 |     |     |     |
| GGT | GCA | CAC | AAC | CTC | GAC | TGC | GTG | CTA | AGA | GAG | GGT | GCC | ACG | CTA | TTC | 1740 |
| Gly | Ala | His | Asn | Leu | Asp | Cys | Val | Leu | Arg | Glu | Gly | Ala | Thr | Leu | Phe |     |
|     | 545 |     |     |     | 550 |     |     |     |     | 555 |     |     |     |     |     |     |
| CCT | GTG | GTC | ATT | ACG | ACA | GTG | GAA | GAC | GCC | ATG | ACA | CCC | AAA | GCA | CTG | 1788 |
| Pro | Val | Val | Ile | Thr | Thr | Val | Glu | Asp | Ala | Met | Thr | Pro | Lys | Ala | Leu |     |
| 560 |     |     |     |     | 565 |     |     |     |     | 570 |     |     |     |     | 575 |     |
| AAC | AGC | AAA | ATG | TTT | GCT | GTC | ATT | GAA | GGC | GTG | CGA | GAA | GAC | CTC | CAA | 1836 |
| Asn | Ser | Lys | Met | Phe | Ala | Val | Ile | Glu | Gly | Val | Arg | Glu | Asp | Leu | Gln |     |
|     |     |     |     | 580 |     |     |     |     | 585 |     |     |     |     | 590 |     |     |
| CCT | CCA | TCT | CAA | AGA | GGA | TCC | TTC | ATA | CGA | ACT | CTC | TCC | GGA | CAC | AGA | 1884 |
| Pro | Pro | Ser | Gln | Arg | Gly | Ser | Phe | Ile | Arg | Thr | Leu | Ser | Gly | His | Arg |     |
|     |     |     | 595 |     |     |     |     | 600 |     |     |     |     | 605 |     |     |     |
| GTC | TAT | GGA | TAT | GCT | CCA | GAT | GGG | GTA | CTT | CCA | CTG | GAG | ACT | GGG | AGA | 1932 |
| Val | Tyr | Gly | Tyr | Ala | Pro | Asp | Gly | Val | Leu | Pro | Leu | Glu | Thr | Gly | Arg |     |
|     |     | 610 |     |     |     |     | 615 |     |     |     |     | 620 |     |     |     |     |
| GAC | TAC | ACC | GTT | GTC | CCA | ATA | GAT | GAT | GTC | TGG | GAC | GAC | AGC | ATT | ATG | 1980 |
| Asp | Tyr | Thr | Val | Val | Pro | Ile | Asp | Asp | Val | Trp | Asp | Asp | Ser | Ile | Met |     |
|     | 625 |     |     |     | 630 |     |     |     |     | 635 |     |     |     |     |     |     |
| CTG | TCC | AAG | GAC | CCC | ATA | CCT | CCT | ATT | GTG | GGA | AAC | AGT | GGA | AAC | CTA | 2028 |
| Leu | Ser | Lys | Asp | Pro | Ile | Pro | Pro | Ile | Val | Gly | Asn | Ser | Gly | Asn | Leu |     |
| 640 |     |     |     |     | 645 |     |     |     |     | 650 |     |     |     |     | 655 |     |
| GCC | ATA | GCT | TAC | ATG | GAT | GTG | TTT | CGA | CCC | AAA | GTC | CCC | ATC | CAT | GTG | 2076 |
| Ala | Ile | Ala | Tyr | Met | Asp | Val | Phe | Arg | Pro | Lys | Val | Pro | Ile | His | Val |     |
|     |     |     |     | 660 |     |     |     |     | 665 |     |     |     |     | 670 |     |     |
| GCC | ATG | ACG | GGA | GCC | CTC | AAC | GCT | TGT | GGC | GAG | ATT | GAG | AAA | ATA | AGC | 2124 |
| Ala | Met | Thr | Gly | Ala | Leu | Asn | Ala | Cys | Gly | Glu | Ile | Glu | Lys | Ile | Ser |     |
|     |     |     | 675 |     |     |     |     | 680 |     |     |     |     | 685 |     |     |     |
| TTC | AGA | AGC | ACC | AAG | CTC | GCC | ACC | GCA | CAC | CGG | CTT | GGC | CTC | AAG | TTG | 2172 |
| Phe | Arg | Ser | Thr | Lys | Leu | Ala | Thr | Ala | His | Arg | Leu | Gly | Leu | Lys | Leu |     |
|     |     | 690 |     |     |     |     | 695 |     |     |     |     | 700 |     |     |     |     |
| GCT | GGT | CCC | GGA | GCA | TTC | GAT | GTA | AAC | ACC | GGG | CCC | AAC | TGG | GCA | ACG | 2220 |
| Ala | Gly | Pro | Gly | Ala | Phe | Asp | Val | Asn | Thr | Gly | Pro | Asn | Trp | Ala | Thr |     |
|     | 705 |     |     |     | 710 |     |     |     |     | 715 |     |     |     |     |     |     |
| TTC | ATC | AAA | CGT | TTC | CCT | CAC | AAT | CCA | CGC | GAC | TGG | GAC | AGG | CTC | CCC | 2268 |
| Phe | Ile | Lys | Arg | Phe | Pro | His | Asn | Pro | Arg | Asp | Trp | Asp | Arg | Leu | Pro |     |
| 720 |     |     |     |     | 725 |     |     |     |     | 730 |     |     |     |     | 735 |     |
| TAC | CTT | AAC | CTT | CCA | TAC | CTT | CCA | CCC | AAT | GCA | GGA | CGC | CAG | TAC | CAC | 2316 |
| Tyr | Leu | Asn | Leu | Pro | Tyr | Leu | Pro | Pro | Asn | Ala | Gly | Arg | Gln | Tyr | His |     |
|     |     |     |     | 740 |     |     |     |     | 745 |     |     |     |     | 750 |     |     |
| CTT | GCC | ATG | GCT | GCA | TCA | GAG | TTC | AAA | GAG | ACC | CCT | GAA | CTC | GAG | AGC | 2364 |
| Leu | Ala | Met | Ala | Ala | Ser | Glu | Phe | Lys | Glu | Thr | Pro | Glu | Leu | Glu | Ser |     |
|     |     |     | 755 |     |     |     |     | 760 |     |     |     |     | 765 |     |     |     |
| GCC | GTA | AGA | GCC | ATG | GAA | GCA | GCT | GCC | AAT | GTG | GAC | CCA | CTG | TTC | CAA | 2412 |
| Ala | Val | Arg | Ala | Met | Glu | Ala | Ala | Ala | Asn | Val | Asp | Pro | Leu | Phe | Gln |     |
|     |     | 770 |     |     |     |     | 775 |     |     |     |     | 780 |     |     |     |     |
| TCT | GCA | CTC | AGT | GTG | TTC | ATG | TGG | CTG | GAA | GAG | AAT | GGG | ATT | GTG | ACT | 2460 |
| Ser | Ala | Leu | Ser | Val | Phe | Met | Trp | Leu | Glu | Glu | Asn | Gly | Ile | Val | Thr |     |
| 785 |     |     |     |     | 790 |     |     |     |     | 795 |     |     |     |     |     |     |
| GAC | ATG | GCC | AAC | TTC | GCA | CTC | AGC | GAC | CCG | AAT | GCC | CAT | CGG | ATG | CGA | 2508 |
| Asp | Met | Ala | Asn | Phe | Ala | Leu | Ser | Asp | Pro | Asn | Ala | His | Arg | Met | Arg |     |
| 800 |     |     |     |     | 805 |     |     |     |     | 810 |     |     |     |     | 815 |     |
| AAT | TTT | CTT | GCA | AAC | GCA | CCA | CAA | GCA | GGC | AGC | AAG | TCG | CAA | AGG | GCC | 2556 |
| Asn | Phe | Leu | Ala | Asn | Ala | Pro | Gln | Ala | Gly | Ser | Lys | Ser | Gln | Arg | Ala |     |
|     |     |     |     | 820 |     |     |     |     | 825 |     |     |     |     | 830 |     |     |
| AAG | TAC | GGG | ACA | GCA | GGC | TAC | GGA | GTG | GAG | GCC | CGG | GGC | CCC | ACA | CCA | 2604 |
| Lys | Tyr | Gly | Thr | Ala | Gly | Tyr | Gly | Val | Glu | Ala | Arg | Gly | Pro | Thr | Pro |     |
|     |     |     | 835 |     |     |     |     | 840 |     |     |     |     | 845 |     |     |     |
| GAG | GAA | GCA | CAG | AGG | GAA | AAA | GAC | ACA | CGG | ATC | TCA | AAG | AAG | ATG | GAG | 2652 |
| Glu | Glu | Ala | Gln | Arg | Glu | Lys | Asp | Thr | Arg | Ile | Ser | Lys | Lys | Met | Glu |     |

|  |  |  |  |  |  |  |  |  |  |  |  |  |  |  |  |
|---|---|---|---|---|---|---|---|---|---|---|---|---|---|---|---|
|  | 850 |  |  |  |  | 855 |  |  |  |  | 860 |  |  |  |  |
| ACC | ATG | GGC | ATC | TAC | TTT | GCA | ACA | CCA | GAA | TGG | GTA | GCA | CTC | AAT | GGG |
| Thr | Met | Gly | Ile | Tyr | Phe | Ala | Thr | Pro | Glu | Trp | Val | Ala | Leu | Asn | Gly |
|  | 865 |  |  |  | 870 |  |  |  |  | 875 |  |  |  |  |  |

```
ACC ATG GGC ATC TAC TTT GCA ACA CCA GAA TGG GTA GCA CTC AAT GGG    2700
Thr Met Gly Ile Tyr Phe Ala Thr Pro Glu Trp Val Ala Leu Asn Gly
    865             870             875

CAC CGC GGG CCA AGC CCC GGC CAG CTA AAG TAC TGG CAG AAC ACA CGA    2748
His Arg Gly Pro Ser Pro Gly Gln Leu Lys Tyr Trp Gln Asn Thr Arg
880             885             890             895

GAA ATA CCG GAC CCA AAC GAG GAC TAT CTA GAC TAC GTG CAT GCA GAG    2796
Glu Ile Pro Asp Pro Asn Glu Asp Tyr Leu Asp Tyr Val His Ala Glu
            900             905             910

AAG AGC CGG TTG GCA TCA GAA GAA CAA ATC CTA AGG GCA GCT ACG TCG    2844
Lys Ser Arg Leu Ala Ser Glu Glu Gln Ile Leu Arg Ala Ala Thr Ser
        915             920             925

ATC TAC GGG GCT CCA GGA CAG GCA GAG CCA CCC CAA GCT TTC ATA GAC    2892
Ile Tyr Gly Ala Pro Gly Gln Ala Glu Pro Pro Gln Ala Phe Ile Asp
        930             935             940

GAA GTT GCC AAA GTC TAT GAA ATC AAC CAT GGA CGT GGC CCA AAC CAA    2940
Glu Val Ala Lys Val Tyr Glu Ile Asn His Gly Arg Gly Pro Asn Gln
    945             950             955

GGA CAG ATG AAA GAT CTG CTC TTG ACT GCG ATG GAG ATG AAG CAT CGC    2988
Gly Gln Met Lys Asp Leu Leu Leu Thr Ala Met Glu Met Lys His Arg
960             965             970             975

AAT CCC AGG CGG GCT CCA CCA AAG CCC AAG CCA AAA CCC AAT GCT CCA    3036
Asn Pro Arg Arg Ala Pro Pro Lys Pro Lys Pro Lys Pro Asn Ala Pro
            980             985             990

ACA CAG AGA CCC CCT GGT CGG CTG GGC CGC TGG ATC AGG ACT GTC TCT    3084
Thr Gln Arg Pro Pro Gly Arg Leu Gly Arg Trp Ile Arg Thr Val Ser
        995             1000            1005

GAT GAG GAC CTT GAG TGAGGCTCCT GGGAGTCTCC CGACACCACC CGCGCAGGCG    3139
Asp Glu Asp Leu Glu
        1010

TGGACACCAA TTCGGCCTTA CAACATCCCA AATTGGATCC G                      3180
```

( 2 ) INFORMATION FOR SEQ ID NO:2:

( i ) SEQUENCE CHARACTERISTICS:
        ( A ) LENGTH: 1012 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Asn Leu Gln Asp Gln Thr His Gln Ile Val Pro Phe Ile Arg
 1               5                  10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Ser Gly Asn Tyr
 65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125
```

-continued

| | | | | | | | | | | | | | | |
|---|---|---|---|---|---|---|---|---|---|---|---|---|---|---|
| Phe | Gln | Gly | Ser | Leu | Ser | Glu | Leu | Thr | Asp | Val | Ser | Tyr | Asn | Gly | Leu |
| | 130 | | | | 135 | | | | | 140 | | | | | |
| Met | Ser | Ala | Thr | Ala | Asn | Ile | Asn | Asp | Lys | Ile | Gly | Asn | Val | Leu | Val |
| 145 | | | | | 150 | | | | | 155 | | | | | 160 |
| Gly | Glu | Gly | Val | Thr | Val | Leu | Ser | Leu | Pro | Thr | Ser | Tyr | Asp | Leu | Gly |
| | | | | 165 | | | | | 170 | | | | | 175 | |
| Tyr | Val | Arg | Leu | Gly | Asp | Pro | Ile | Pro | Ala | Ile | Gly | Leu | Asp | Pro | Lys |
| | | | 180 | | | | | 185 | | | | | 190 | | |
| Met | Val | Ala | Thr | Cys | Asp | Ser | Ser | Asp | Arg | Pro | Arg | Val | Tyr | Thr | Ile |
| | | | 195 | | | | 200 | | | | | 205 | | | |
| Thr | Ala | Ala | Asp | Asn | Tyr | Gln | Phe | Ser | Ser | Gln | Tyr | Gln | Thr | Gly | Gly |
| | 210 | | | | | 215 | | | | | 220 | | | | |
| Val | Thr | Ile | Thr | Leu | Phe | Ser | Ala | Asn | Ile | Asp | Ala | Ile | Thr | Ser | Leu |
| 225 | | | | | 230 | | | | | 235 | | | | | 240 |
| Ser | Val | Gly | Gly | Glu | Leu | Val | Phe | Lys | Thr | Ser | Val | Gln | Ser | Leu | Val |
| | | | | 245 | | | | | 250 | | | | | 255 | |
| Leu | Gly | Ala | Thr | Ile | Tyr | Leu | Ile | Gly | Phe | Asp | Gly | Thr | Ala | Val | Ile |
| | | | 260 | | | | | 265 | | | | | 270 | | |
| Thr | Arg | Ala | Val | Ala | Ala | Asn | Asn | Gly | Leu | Thr | Ala | Gly | Ile | Asp | Asn |
| | | 275 | | | | | 280 | | | | | 285 | | | |
| Leu | Met | Pro | Phe | Asn | Leu | Val | Ile | Pro | Thr | Asn | Glu | Ile | Thr | Gln | Pro |
| | 290 | | | | | 295 | | | | | 300 | | | | |
| Ile | Thr | Ser | Ile | Ile | Leu | Glu | Ile | Val | Thr | Ser | Lys | Ser | Asp | Gly | Gln |
| 305 | | | | | 310 | | | | | 315 | | | | | 320 |
| Ala | Gly | Glu | Gln | Met | Ser | Trp | Ser | Ala | Ser | Gly | Ser | Leu | Ala | Val | Thr |
| | | | | 325 | | | | | 330 | | | | | 335 | |
| Ile | His | Gly | Gly | Asn | Tyr | Pro | Gly | Ala | Leu | Arg | Pro | Val | Thr | Leu | Val |
| | | | 340 | | | | | 345 | | | | | 350 | | |
| Ala | Tyr | Glu | Arg | Val | Ala | Thr | Gly | Ser | Val | Val | Thr | Val | Ala | Gly | Val |
| | | | 355 | | | | | 360 | | | | | 365 | | |
| Ser | Asn | Phe | Glu | Leu | Ile | Pro | Asn | Pro | Glu | Leu | Ala | Lys | Asn | Leu | Val |
| | | | 370 | | | | | 375 | | | | | 380 | | |
| Thr | Glu | Tyr | Gly | Arg | Phe | Asp | Pro | Gly | Ala | Met | Asn | Tyr | Thr | Lys | Leu |
| 385 | | | | | 390 | | | | | 395 | | | | | 400 |
| Ile | Leu | Ser | Glu | Arg | Asp | His | Leu | Gly | Ile | Lys | Thr | Val | Trp | Pro | Thr |
| | | | | 405 | | | | | 410 | | | | | 415 | |
| Arg | Glu | Tyr | Thr | Asp | Phe | Arg | Glu | Tyr | Phe | Met | Glu | Val | Ala | Asp | Leu |
| | | | 420 | | | | | 425 | | | | | 430 | | |
| Asn | Ser | Pro | Leu | Lys | Ile | Ala | Gly | Ala | Phe | Gly | Phe | Lys | Asp | Ile | Ile |
| | | | 435 | | | | | 440 | | | | | 445 | | |
| Arg | Ala | Ile | Arg | Arg | Ile | Ala | Val | Pro | Val | Val | Ser | Thr | Leu | Phe | Pro |
| | 450 | | | | | 455 | | | | | 460 | | | | |
| Pro | Ala | Ala | Pro | Leu | Ala | His | Ala | Ile | Gly | Glu | Gly | Val | Asp | Tyr | Leu |
| 465 | | | | | 470 | | | | | 475 | | | | | 480 |
| Leu | Gly | Asp | Glu | Ala | Gln | Ala | Ala | Ser | Gly | Thr | Ala | Arg | Ala | Ala | Ser |
| | | | | 485 | | | | | 490 | | | | | 495 | |
| Gly | Lys | Ala | Arg | Ala | Ala | Ser | Gly | Arg | Ile | Arg | Gln | Leu | Thr | Leu | Ala |
| | | | 500 | | | | | 505 | | | | | 510 | | |
| Ala | Asp | Lys | Gly | Tyr | Glu | Val | Val | Ala | Asn | Leu | Phe | Gln | Val | Pro | Gln |
| | | 515 | | | | | 520 | | | | | 525 | | | |
| Asn | Pro | Val | Val | Asp | Gly | Ile | Leu | Ala | Ser | Pro | Gly | Ile | Leu | Arg | Gly |
| | 530 | | | | | 535 | | | | | 540 | | | | |
| Ala | His | Asn | Leu | Asp | Cys | Val | Leu | Arg | Glu | Gly | Ala | Thr | Leu | Phe | Pro |
| 545 | | | | | 550 | | | | | 555 | | | | | 560 |

| | | | | | | | | | | | | | | |
|---|---|---|---|---|---|---|---|---|---|---|---|---|---|---|
| Val | Val | Ile | Thr | Thr 565 | Val | Glu | Asp | Ala | Met 570 | Thr | Pro | Lys | Ala | Leu 575 | Asn |
| Ser | Lys | Met | Phe 580 | Ala | Val | Ile | Glu | Gly 585 | Val | Arg | Glu | Asp | Leu 590 | Gln | Pro |
| Pro | Ser | Gln 595 | Arg | Gly | Ser | Phe | Ile 600 | Arg | Thr | Leu | Ser | Gly 605 | His | Arg | Val |
| Tyr | Gly 610 | Tyr | Ala | Pro | Asp | Gly 615 | Val | Leu | Pro | Leu | Glu 620 | Thr | Gly | Arg | Asp |
| Tyr 625 | Thr | Val | Val | Pro | Ile 630 | Asp | Asp | Val | Trp | Asp 635 | Asp | Ser | Ile | Met | Leu 640 |
| Ser | Lys | Asp | Pro | Ile 645 | Pro | Pro | Ile | Val | Gly 650 | Asn | Ser | Gly | Asn 655 | Leu | Ala |
| Ile | Ala | Tyr | Met 660 | Asp | Val | Phe | Arg | Pro 665 | Lys | Val | Pro | Ile 670 | His | Val | Ala |
| Met | Thr | Gly 675 | Ala | Leu | Asn | Ala | Cys 680 | Gly | Glu | Ile | Glu | Lys 685 | Ile | Ser | Phe |
| Arg | Ser 690 | Thr | Lys | Leu | Ala | Thr 695 | Ala | His | Arg | Leu | Gly 700 | Leu | Lys | Leu | Ala |
| Gly 705 | Pro | Gly | Ala | Phe | Asp 710 | Val | Asn | Thr | Gly | Pro 715 | Asn | Trp | Ala | Thr | Phe 720 |
| Ile | Lys | Arg | Phe | Pro 725 | His | Asn | Pro | Arg | Asp 730 | Trp | Asp | Arg | Leu | Pro 735 | Tyr |
| Leu | Asn | Leu | Pro 740 | Tyr | Leu | Pro | Pro | Asn 745 | Ala | Gly | Arg | Gln | Tyr 750 | His | Leu |
| Ala | Met | Ala 755 | Ala | Ser | Glu | Phe | Lys 760 | Glu | Thr | Pro | Glu | Leu 765 | Glu | Ser | Ala |
| Val | Arg 770 | Ala | Met | Glu | Ala | Ala 775 | Ala | Asn | Val | Asp | Pro 780 | Leu | Phe | Gln | Ser |
| Ala 785 | Leu | Ser | Val | Phe | Met 790 | Trp | Leu | Glu | Glu | Asn 795 | Gly | Ile | Val | Thr | Asp 800 |
| Met | Ala | Asn | Phe | Ala 805 | Leu | Ser | Asp | Pro | Asn 810 | Ala | His | Arg | Met 815 | Arg | Asn |
| Phe | Leu | Ala | Asn 820 | Ala | Pro | Gln | Ala | Gly 825 | Ser | Lys | Ser | Gln 830 | Arg | Ala | Lys |
| Tyr | Gly | Thr 835 | Ala | Gly | Tyr | Gly | Val 840 | Glu | Ala | Arg | Gly | Pro 845 | Thr | Pro | Glu |
| Glu | Ala 850 | Gln | Arg | Glu | Lys | Asp 855 | Thr | Arg | Ile | Ser | Lys 860 | Lys | Met | Glu | Thr |
| Met 865 | Gly | Ile | Tyr | Phe | Ala 870 | Thr | Pro | Glu | Trp | Val 875 | Ala | Leu | Asn | Gly | His 880 |
| Arg | Gly | Pro | Ser | Pro 885 | Gly | Gln | Leu | Lys | Tyr 890 | Trp | Gln | Asn | Thr | Arg 895 | Glu |
| Ile | Pro | Asp | Pro 900 | Asn | Glu | Asp | Tyr | Leu 905 | Asp | Tyr | Val | His | Ala 910 | Glu | Lys |
| Ser | Arg | Leu 915 | Ala | Ser | Glu | Glu | Gln 920 | Ile | Leu | Arg | Ala | Ala 925 | Thr | Ser | Ile |
| Tyr | Gly 930 | Ala | Pro | Gly | Gln | Ala 935 | Glu | Pro | Pro | Gln | Ala 940 | Phe | Ile | Asp | Glu |
| Val 945 | Ala | Lys | Val | Tyr | Glu 950 | Ile | Asn | His | Gly | Arg 955 | Gly | Pro | Asn | Gln | Gly 960 |
| Gln | Met | Lys | Asp | Leu 965 | Leu | Leu | Thr | Ala | Met 970 | Glu | Met | Lys | His | Arg 975 | Asn |
| Pro | Arg | Arg | Ala | Pro | Pro | Lys | Pro | Lys | Pro | Lys | Pro | Asn | Ala | Pro | Thr |

| | 980 | | | | 985 | | | | | 990 | | | |
|---|---|---|---|---|---|---|---|---|---|---|---|---|---|
| Gln Arg Pro | Pro | Gly | Arg | Leu | Gly | Arg | Trp | Ile | Arg | Thr | Val | Ser | Asp |
| | 995 | | | | 1000 | | | | | 1005 | | | |
| Glu Asp Leu Glu |
| 1010 |

ATTENUATED, LIVE VACCINE FOR DELAWARE STRAIN IBDV

This application is a Continuation-in-Part of U.S. patent application Ser. No. 07/423,758, filed Oct. 18, 1989, now abandoned.

BACKGROUND OF THE INVENTION

1. Field of the Invention

The invention pertains to a vaccine prepared from a live, but attenuated virus of the Delaware strain inducing infectious bursal disease in chickens. Specifically, a vaccine is prepared by screening potential attenuated virus candidates with a non-neutralizing specific monoclonal antibody. Further, a highly specific neutralizing monoclonal antibody is provided as an alternative, effective vaccine.

2. Background of the Prior Art

In the inventors' related applications, including U.S. patent application Ser. No. 07/423,752, entitled MONOCLONAL ANTIBODIES FOR INFECTIOUS BURSAL DISEASE, VACCINES AND ASSAYS FOR USE THEREWITH, which in turn is a CIP application of U.S. application Ser. No. 07/061,083, now U.S. Pat. No. 4,956,452 and U.S. application Ser. No. 07/227,311, now U.S. Pat. No. 5,064,646 the development and study of a large number of monoclonal antibodies (Mab) specific for various strains of infectious bursal disease is discussed. As related in the above-cited U.S. application Ser. No. 07/423,752, the entire content of which is incorporated herein by reference, a panel of antibodies has been developed, each specific to a particular type of infectious bursal disease virus. That virus has been, by means of antibody assays, categorized into three separate classifications, classic, Delaware and GLS. At the time of filing of this application, the Delaware strain, of all pure strains, appears to be the dominant infectious bursal disease virus in the Eastern United States. Certainly, it is a substantial and continuing threat to the U.S. poultry industry.

Wild-type Delaware IBDV have been known for some time, and are commercially available. There are a number of vaccines for this Delaware-type IBDV commercially available, including both "killed" and "live" vaccines. A killed vaccine is prepared by culturing the virus itself, in e.g., chicken eggs and the like, and subsequently "killing" the virus by heat, chemical treatment and the like. In a live vaccine, the virus is present in a living form, but has been attenuated to reduce or eliminate its virulency, by serial passage through cell culturing and the like. Thus, the "virus" component of a live vaccine is attenuated. Methods for preparation thereof are known in the art, and do not constitute, per se, an aspect of this invention. No currently available vaccine for wild-type Delaware IBDV is based on or comprises a non-virus active element, such as a monoclonal antibody.

During the analysis and categorization of IBDV in the United States, all commercially available live, attenuated Delaware strain vaccines were assayed. One of the monoclonal antibodies used in that assay is designated BK9, and is expressed by the hybridomal cell line deposited at the ATCC under deposit number HB-10157.

It is apparent that in order to provide adequate coverage and protection against the Delaware strain infection, a live, attenuated vaccine must contain a virus that will produce antibodies recognizing the wild-type Delaware IBDV. That is, in the process of attenuation, the marker characteristics of the wild-type Delaware virus strain must not be lost. Surprisingly, in the course of testing commercially available vaccines, not one was demonstrated to bear the BK9 Mab marker, and thus not truly wild-type. Vaccines employing this type of virus will not, in fact, generate antibodies providing effective protection against wild-type Delaware IBDV infection. Thus, it remains a pressing need in the industry to provide a live, attenuated vaccine for Delaware IBDV.

Alternatively, it is known that for certain IBDV, vaccines can be prepared from monoclonal antibodies (Mab) which neutralize the virus. See, in particular, U.S. Pat. No. 4,956,452. It is a continuing goal to provide such Mab which neutralize the Delaware strain IBDV, and provide a vaccine based thereon.

SUMMARY OF THE INVENTION

The above goal, and others made clear by the invention disclosure set forth below, has been met by identification of the fact that the wild-type Delaware virus does not replicate well in serial cell culturing. Thus, live, attenuated viruses obtained by serial passaging of the wild-type Delaware strain IBDV frequently lose the IBDV characteristics desirable or necessary to induce the production of effective antibodies against the parental virus. A Delaware virus which lacks the BK9 Mab marker, i.e., to which that monoclonal antibody will not bind, will not or may not confer as effective protection, in a vaccine against the wild type.

When attenuating a wild-type Delaware IBDV, it is highly unlikely that any given adapt (the result of serial passaging) will retain the BK9 marker, and so provide effective coverage. The odds, in fact, on successful passaging are quite small. Therefore, adapts, as produced, must be screened for retention of the Delaware marker, by antigen capture enzyme linked immunosorbent assay (AC-ELISA) assay using the BK9 marker. As reflected in copending application, Attorney Docket Number 2284-018-0 CIP, the binding of the BK9 marker is a positive indication of the presence of the wild type Delaware strain.

A neutralizing Mab has been developed against the wild-type Delaware strain of IBDV. The antibody has been deposited and extensively mapped.

BRIEF DESCRIPTION OF THE DRAWING

FIG. 1–1e is a rendering of the complete nucleotide and deduced amino acid sequence (SEQ ID NOS: 1–2) of the Delaware IBDV structural protein(s) that is recognized by the Monoclonal Antibody 67.

DETAILED DESCRIPTION OF THE INVENTION:

Six different cell culture adapted (i.e., chicken embryo fibroblast and the like) attenuated viruses were prepared from wild-type Delaware IBDV. Each was prepared by serial passaging through cell culture processes, conventional in the industry. Alternate methods of producing attenuated viruses, including cloning of the virus with deletion of nucleic acid sequences and site-directed mutagenesis, are also known, and are embraced in the invention. Of the six adapts prepared, five, when tested with the monoclonal antibody expressed by HB-10157 yielded negative results, that is, that had lost the BK9 antibody marker. Such viruses, although attenuated, will not or may not induce the production of antibodies effective in preventing Delaware IBDV infection.

The sixth adapt did indeed react positively with the BK9 monoclonal antibody, thus indicating that this attenuated virus still maintained an essential characteristics of a wild-type Delaware IBDV, and as prepared in a vaccine, should induce the production of antibody effective against wild-type Delaware IBDV infection. This sixth adapt is currently available from the University of Maryland or Intervet America and can be continuously monitored and maintained in chicken origin or vero cell lines located at Avrum Gudelsky Center, College of Veterinary Medicine, University of Maryland. However, it should be noted that access to this virus or these cell lines is not necessary to practice the invention. Specifically, the adapts retaining the BK9 marker, and thus providing effective vaccines, occur randomly, with a low probability for the given adapt, as discussed above. There appears to be a portion of the wild-type Delaware IBDV genomic population which does not replicate well during serial passage. However, the odds on successful reproduction of an attenuated virus, given appropriate screening measures is quite high, if a large enough family of adapts is made. Thus, one of ordinary skill in the art, practicing a plurality of serial passages, need only screen the results with the BK9 Mab, available from the deposit, made under Budapest Treaty conditions, in order to practice this invention.

Identification of the virus presence and confirmation of its virulence, is conducted in a fashion identical to that set forth in the copending application U.S. Application Ser. No. 07/423,752, incorporated herein by reference. Given the monoclonal antibody, these procedures are routine.

The vaccines themselves may be prepared by simple incorporation of the selected virus, confirmed by screening, and suspending or mixing it in a carrier. Appropriate dosage values can be determined through team trial and error techniques, sampling for the production of antibodies in the treated poultry individual. In general, dosage ranges will vary in a physiologically acceptable carrier, such as buffered saline, cell culture medium, Mareti's virus vaccine diluent, etc. The dosage is determined by the ability of the virus to replicate in the chicken and provide effective immunity with minimal pathologic damage.

Applicants have also developed a Mab, designated Mab 67, which neutralizes the wild-type Delaware strain IBDV. The murine monoclonal antibody is specific only for the Delaware-type virus, and does not neutralize or bind to other recognized IBDV viruses. Mab 67 does not bind to, or neutralize any of the currently available live or live-attenuated vaccine viruses which are licensed or currently available, intended to confer protection against Delaware-type IBDV. This further confirms the inadequacy of existing virus-based vaccines to confer protection against Delaware-type infection.

The monoclonal antibody was developed according to the method set forth in U.S. Pat. No. 4,956,452. Specifically, hybridoma cell lines were prepared according to standard procedure beginning with BALB/c mice, immunized with the Delaware virus strain, after purification. Hybridomas were prepared therefrom, and the resulting cell lines were assayed, through an enzyme-linked immunosorbent assay (ELISA) to identify those lines secreting an antibody that binds to at least one strain. The resulting cell line was cloned again, and injected into pristane primed mice, to produce ascitic fluid with higher titer values. Specific details as to the propagation of the IBDV strains used, production of the hybridomas, the ELISA employed, and the virus neutralization tests are set forth in U.S. Pat. No. 4,956,452, beginning at column 3, line 64 and continuing on to column 5, line 68. The disclosure of this patent is incorporated herein by reference. The hybridoma cell line expressing Mab 67 has been deposited under Accession No. ATCC-HB11122, deposited at the ATCC by David Snyder on Sep. 15, 1992. Further, the cell lines are continuously available from Avrum Gudelsky Center, College of Veterinary Medicine, University of Maryland. This Mab can be used not only as an assay to determine the presence of the Delaware-type IBDV, but in addition to the virus-based vaccine disclosed above, can be employed to prepare a vaccine conferring challenge protection against Delaware-type IBDV. To achieve temporary passive immunization at a uniform, standardized level, and to augment any maternally derived levels against Delaware-type IBDV field infection, one-day old chicks should be vaccinated with a vaccine comprising a pharmacologically acceptable carrier such as a phosphate buffered saline, cell culture medium, Mareti's virus vaccine diluent, etc., in which is present an amount of Mab 67 effective to provide enhanced protection for a period of time which allows the chicks to become more immunologically competent (about two-three weeks). The necessary level of protection can be conferred by a single dose of the vaccine administered to day-old chicks having a Mab concentration of between 1 microgram and 1 milligram, or repeated vaccinations having a smaller effective dose, but carried out over time. If repeated vaccinations are used, the dosage level should range within 10 micrograms to 1 milligram. The concentration level needed to vaccinate older chickens is expected to increase with the weight of the bird. Other administration protocols can be developed by those of skill in the art without the exercise of inventive skill.

It should be noted that in general, the pharmacologically acceptable carriers to be used with the virus-based vaccine discussed above can also be used in conjunction with the Mab-based vaccine addressed herein.

FIGS. 1–1E contains a full recitation of the nucleotide sequence (SEQ ID NO: 1) for the gene responsible for the expression of Delaware IBDV structural protein(s) recognized by Mab 67. Presented together with this information in FIGS. 1–1E is the amino acid sequence (SEQ ID NO: 2) for the Delaware IBDV protein(s) which will be recognized by Mab 67. As noted above, it is apparent that the virus quickly loses, in serial passage, its identifying characteristics, and accordingly, wholesale modification of the Mab, from a synthetic or site-specific mutagenesis aspect, may impair or destroy the antibody's ability to neutralize the virus. Nonetheless, based on the length of the amino acid required for the binding of the antibody, and studies applied to similar materials, it is expected that up to 10 percent of the amino acids of the structure can be modified or deleted, and up to 25 percent of the nucleotide sequence replaced or modified, particularly at the ends of the sequence, without loss of the binding and neutralizing ability of Mab 67. In particular, small modifications which do not affect conformal (quaternary) structure will not impede binding. Such modifications are clearly contemplated as one aspect of this invention.

Obviously, numerous modifications and variations of the present invention are possible in light of the above teachings. It is therefore to be understood that within the scope of the appended claims, the invention may be alternatively described or practiced otherwise than as specifically described herein.

What is claimed is:

1. A live, attenuated infectious bursal disease virus (IBDV) capable of inducing antibodies to wild-type Delaware IBDV in poultry when administered thereto, but sufficiently attenuated so as not to induce infectious bursal disease in said treated poultry, said live, attenuated virus bearing a BK9 monoclonal antibody marker.

2. The virus of claim 1 which is capable of inducing antibodies protective against wild-type Delaware IBDV infection.

3. A vaccine comprising the virus of claim 2 and a pharmaceutically acceptable carrier.

4. A method of vaccinating poultry against wild-type Delaware IBDV comprising administering to said poultry the vaccine of claim 3.

5. A monoclonal antibody which neutralizes wild-type Delaware IBDV, designated Mab 67.

6. A hybridoma cell line which produces the monoclonal antibody of claim 5, designated ATCC-HB11122.

7. A vaccine for passive immunization of poultry against Delaware-type IBDV, comprising a pharmaceutically acceptable carrier and an effective amount of the monoclonal antibody of claim 5.

8. A method for passive immunization of poultry against Delaware-type IBDV, comprising administering the vaccine of claim 7 to said poultry.

* * * * *

UNITED STATES PATENT AND TRADEMARK OFFICE
CERTIFICATE OF CORRECTION

PATENT NO. : 5,632,989
DATED : May 27, 1997
INVENTOR(S) : David B. SNYDER, et al.

It is certified that error appears in the above-indentified patent and that said Letters Patent is hereby corrected as shown below:

On the title page and the top of column 1, item [63], the Related U.S. Application Data should read:

--Continuation-in-part of Ser. No. 423,752, Oct. 18, 1989, abandoned, which is a continuation-in-part of Ser. No. 61,083, Jun. 12, 1987, Pat. No. 4,956,452, which is a continuation-in-part of Ser. No. 227,311, Aug. 2, 1988, Pat. No. 5,064,646.--

Signed and Sealed this

Fourteenth Day of October, 1997

Attest:

BRUCE LEHMAN

Attesting Officer

Commissioner of Patents and Trademarks